(12) United States Patent
Saenziturriaga

(10) Patent No.: US 8,940,693 B2
(45) Date of Patent: Jan. 27, 2015

(54) PROTEIN FOR THE IMMUNOCASTRATION FOR MAMMALS

(75) Inventor: Leonardo Enrique Saenziturriaga, Santiago (CL)

(73) Assignee: Universidad de Chile, Santiago (CL)

( * ) Notice: Subject to any disclaimer, the term of this patent is extended or adjusted under 35 U.S.C. 154(b) by 146 days.

(21) Appl. No.: 13/262,265

(22) PCT Filed: Apr. 14, 2010

(86) PCT No.: PCT/CL2010/000014
§ 371 (c)(1),
(2), (4) Date: Dec. 20, 2011

(87) PCT Pub. No.: WO2010/118547
PCT Pub. Date: Oct. 21, 2010

(65) Prior Publication Data
US 2012/0093846 A1    Apr. 19, 2012

(30) Foreign Application Priority Data
Apr. 15, 2009    (CL) .................................... 900-2009

(51) Int. Cl.
*A61K 38/09* (2006.01)
*C07K 7/23* (2006.01)
*A61K 39/00* (2006.01)
*C07K 7/08* (2006.01)

(52) U.S. Cl.
CPC ............... *A61K 39/0006* (2013.01); *C07K 7/08* (2013.01); *C07K 7/23* (2013.01); *A61K 2039/6031* (2013.01)
USPC .......... 514/10.3; 514/21.3; 530/313; 530/324

(58) Field of Classification Search
None
See application file for complete search history.

(56) References Cited

PUBLICATIONS

Saenz, L. et al., "Chitosan formulations improve the immunogenicity of a GnRH-1 peptide based vaccine," Interntational Journal of Pharmaceutics, 369(1-2):64-71 (2009), available on-line Nov. 12, 2008.

*Primary Examiner* — Christine J Saoud
(74) *Attorney, Agent, or Firm* — Abelman, Frayne & Schwab

(57) ABSTRACT

Fusion protein for immunocastration (Sequences 1a and 1b) that comprises the primary amino acid sequence of the gonadotrophin-liberating protein fused to a theoretical sequence:

Sequence 1a NH2-QHWSYGLRPGGPPFSGGGGPPFSA-COOH (SEQ ID NO: 1)

Sequence 1b NH2-GPPFSGGGGPPFSAQHWSYGLRPG-COOH (SEQ ID NO: 2);

DNA sequences coding for said fusion protein; vaccine comprising said fusion protein; use of the fusion protein for mammal immunocastration; process for producing the vaccine; process for preparing the fusion protein that comprises fusing the amino acid sequence of the gonadotrophin-liberating hormone (GnRH-I) to a theoretical glycosilable sequence having immunogenic activity that does not include pathogen or "carrier" protein sequences in its structure.

18 Claims, 5 Drawing Sheets

Days after immunization

Days after immunization

PROTEIN FOR THE IMMUNOCASTRATION FOR MAMMALS

RELATED APPLICATIONS

This application is a §371 of PCT/CL2010/000014 filed Apr. 14, 2010, and claims priority from Chilean Patent Application No. 900-2009 filed Apr. 15, 2009, both incorporated by reference in their entirety.

FIELD OF THE INVENTION

The present invention refers to the field of Genetic Engineering and Biotechnology and particularly to the use of a polypeptide that incorporates the amino acid sequence of the gonadotrophin-releasing hormone (GnRH-I) for mammal immunocastration.

BRIEF SUMMARY OF THE INVENTION

The polypeptide of the present invention is a chimeric polypeptide or glycopeptide, formed by fusion of the amino acid sequence of the gonadotrophin-releasing hormone (GnRH-I) or variants thereof, and a non pathogen-derived theoretical sequence that enhances GnRH immunogenicity. The present fusion protein, its glycosilated version, as well as its tandem repetitions, may be used, together with different types of adjuvants, to immunoneutralize the gonadotrophin-releasing hormone (GnRH-I) producing a block in steroidogenesis, oogenesis and spermatogenesis in different animal species.

PRIOR ART COMMENTS

In most animal species, the reproductive capacities of both sexes suffer from temporary cyclic fluctuations as a result of the effects generated by sex hormones on gonads and on the reproductive system in general. Gonadotrophin-releasing hormone or GnRH plays a central part in this process.

The GnRH-I hormone is a decapeptide possessing an amino acid sequence evolutively well preserved and common for most mammals. GnRH-I is liberated from the mesiobasal portion of the hypothalamus and enters into the blood stream, where it induces in the hypophysis liberation of LH and FSH from gonadotroph cells. For several years efforts have been made to generate immunoneutralization of the GnRH-I hormone as a control of steroidogenesis, oogenesis and spermatogenesis. GnRH block with the accompanying reduction of gonadotrophin levels has various applications; thus, in human medicine the reduction of androgen production in patients with prostatic carcinoma has been a treatment target for several years. On the other hand, in veterinary medicine reproductive capability blocking in pets or wild species that may become plagues, with minimum side effects, has been a subject of research and development. In the field of animal breeding, surgical castration of males is a routine procedure to avoid an aggressive sexual behavior or to prevent their flesh from acquiring undesirable organoleptic characteristics through the effect of pheromones. In all these settings, the use of a vaccine capable of blocking GnRH-I hormone function represents an important tool.

The effect of different vaccines against GnRH hormone has been assessed in a great number of animal species, using various types of molecules associated to GnRH, together with different types of adjuvants. Most of these approaches are based on chemical synthesis of haptens linking GnRH to a highly immunogenic molecule such as bovine albumin (BSA), ovalbumin (OVA), tetanic toxoid (TT) or hemocyanin (KLH) (Sad, Chauhan et al. 1993; Beekman, Schaaper et al. 1999; Dunshea, Colantoni et al. 2001; Miller, Gionfriddo et al. 2008). However, a phenomenon of an antigenic dominance has been described, wherein these "carrier" proteins suppress the response to epitopes of the molecule of interest after successive immunizations, in a mechanism of tolerance to the GnRH antigen (Sad, Gupta et al. 1991; Sad, Gupta et al. 1991; Sad, Talwar et al. 1991). Epitope suppression may result from a defect in the hapten presentation by specific B-lymphocytes developing an immune response of the "helper" Type 2 (Th2) (Renjifo, Wolf et al. 1998). The exclusion of epitopes with high antigenicity, as stated in the present invention, reduces the risk of antigenic suppression and supports an immune response in favor of the GnRH antigen, allowing it to be used efficiently in repeated immunizations. Other obstacle to the use of the model of "carrier" proteins is the high cost in antigen synthesis and conjugation.

Recombinant ADN technology has been used to create tandem repeated GnRH molecules, linked to different protein sequences as immunogens for T helper lymphocytes (Hannesdottir, Han et al., 2004; Jinshu, Jingjing et al. 2004; Khan, Ferro et al. 2007; Zhang, Xu et al., 2007; Khan, Ogita et al., 2008). Recombinant proteins with multiple GnRH inserts have shown that immunogenicity is increased with the number of inserted GnRH sequences [15J, and may use this advantage by incorporating in the formulation a greater number of repetitions of the fusion peptide. Multiple epitopes of B or T cells as lipopeptides (Pam3Cys) or different peptide sequences of pathogens such as *Plasmodium falsiparum*, *Mycobacterium*, syncytial respiratory virus or influenza virus, flanking GnRH sequences have been used in various "vaccinal" models and have proved to be effective (Khan, Ferro at al. 2007). In this connection, the present antigen does not incorporate pathogen sequences that may interfere with the liberation of an immune response against the GnRH sequence, since the intergenic sequence used between GnRH repetitions has been designed to improve antigenicity of the GnRH sequence.

In this connection, document OS 2005/0239701 Ai is directed to the use as vaccine of GnRH multimers linked to "carrier" proteins or fragments thereof as bacterial toxins, and to the use of recombinant vectors that incorporate genetic sequences coding for GnRH multimers, by themselves or combined with genetic sequences coding for "carrier" proteins such as titanic toxin C fragment. Said recombinant vectors are directed to modify sexual behavior, fertility or both, in vertebrates through the induction of an immune response that changes the normal physiologic sexual function. The present invention does not incorporate gene or peptide sequences of "carrier" proteins, or corresponds to GnRH multimers by themselves, as it incorporates an intergenic sequence that is not associated with pathogens or "carrier" proteins which operates improving GnRH immunogenicity as an antigen; furthermore, this sequence possesses the potential of being glycosilated when the recombinant protein is expressed in eukaryotic systems capable of making post-translational modifications to proteins.

International publication WO 01/85763 discloses chimeric peptides with immunogenic effectiveness comprising the GnRH hormone sequence and epitope mixtures for T "helper" cells obtained from different pathogens or peptides of known immunogenicity known as the titanic toxin, *Plasmodium falciparum*, or the Measles virus F protein, for the production of anti-GnRH antibody titers.

Generally, in most of the publications that disclose the use of fusion proteins, the method is focused on the use of pathogen sequences that function as T "helper" lymphocyte epitopes, linked to a different number of GnRH repetitions or as in the case of a chemical synthesis, GnRH repetitions linked to an immunogenic molecule per se. An example of this is the document "Use of recombinant gonadotrophin-releasing hormone antigens for immunosterilization of beef heifers", Journal of Animal Science, 2006; 84(2): 343-50, Geary T W, Grings E E, MacNeil M D, de Avila D M, Reeves J J.

A great number of studies have been conducted in pigs and cattle to do research on the use of immunization against GnRH as a method to improve growth rate and the meat product obtained from the animals. See, for example, Adams and Adams, J. Animal Sci. (1992) 70:1691-1698; Caray and Bonneau, C. R. Acad. Sc. Paris (1986) 303:673-676; Chaffaux et al, Recueil de Medicine Veterinaire (1985) 161:133-145; Finnerty et al., J. Repro. Fertil. (1994) 101; 133-343. Castration eliminates the source of endogenous anabolic steroids and feed conversion becomes less efficient, animals need to eat more in order to generate dressed carcasses of the same weight and produce a greater fat cover. To this effect, it has been shown that growth of a non-castrated animal is more efficient than that of a castrated animal. The presence of sexual steroids in the animal acts as natural anabolics, allowing this animal to have a better growth and muscle development performance, thanks to a substantial improvement in feed conversion efficiency. This better efficiency in feed conversion has also positive environmental implications at world level, because it is expressed in a lesser amount of food intake with less pressure on farm lands and a reduction in waste production, and promotes a more sustainable industry using less feed and generating less waste per meat kilogram produced. The target of many of these studies has been to let the animals grow intact as males until they reach the end of the fattening stage, and to subject them after that to an immunologic castration. The use of anti-GnRH vaccines has been proposed as a viable alternative to maintain in production non castrated males that are vaccinated at the end of the productive stage, allowing metabolization of sexual hormones and their associated smell. Several patents that approach this problem have been granted (U.S. Pat. No. 4,975,420 1990; U.S. Pat. No. 6,045,799 2000; U.S. Pat. No. 6,761,890 B1 2004, among others); however, the molecules used therein as antigens are chemical conjugations of the GnRH hormone amino acid sequence to a "carrier" molecule. In this sense, patent application US 2005/0239701 A1 protects the use of a vaccination comprising two doses 4 to 8 weeks before slaughter of the animal to ensure effectiveness of the vaccine, for a short period of time; this limits the application of vaccines against GnRH with an unsatisfactory effectiveness, needing revaccinations to obtain the neutralizing antibody titers to block the hormone effect.

In like manner, the following scientific articles also refer to conjugation of the GnRH sequence and a "carrier" molecule:

Beekman, N. J., W. M. Schaaper, et al. (1999). "Highly immunogenic and fully synthetic peptide-carrier constructs targeting GnRH." *Vaccine* 17 (15-16): 2043-50. It specifies that in order to use peptides as synthetic vaccines, they have to be coupled to a "carrier" protein to make them more immunogenic. However, coupling efficiency between the "carrier" protein and a protein is hard to control with regard to the peptide charge density. As a result, these "carrier" proteins are not very suitable in practice. Attempts have been reported to find "carrier" molecules or delivery systems that allow an easy coupling or peptide incorporation, reproducible charge density and well-defined products. The authors have compared several promising constructs or delivery systems for male pigs immunization using a GnRH peptide in tandem as a branched polylysine construction, a lipo-thioester, a lipo-amide or a KLH conjugate in CFA, and the lipo-amide peptide in an immuno simulator complex (ISCOM). The authors found that lipo-thioester and branched polylysine constructs constituted the most effective "carrier" molecules to induce antibodies anti-GnRH and immunocastration in pigs.

Khan, M. A., K. Ogita, et al. (2008). "Immunization with a plasmid DNA vaccine encoding gonadotrophin-releasing hormone (GnRH-1) and T-helper epitopes in saline suppresses rodent fertility." *Vaccine* 26 (10): 1365-74. It states that research on active immunization against the gonadotrophin-releasing hormone (GnRH-I) is gaining acceptance as a means to control reproduction and behavior in livestock, pets or wild animals. Many studies have described the use of multiple copies of the same peptide aligned and conjugated to a larger "carrier" protein, to enhance the immune response of said peptide. However, the problems that result from suppressing the "carrier" protein epitope have caused a decline of interest in the use of genetic materials that may initiate an optimal immune response. In the study conducted by the authors, a vaccine with 533 DNA base pairs was constructed in pcDNAV5-HisB coding for 18,871 kDa GnRH-I-T-helper-V5 epitopes of fusion proteins. Transfected COSI cells were found with the vaccine construct, that liberate fusion protein into the culture supernatant. The vaccine construct (100 µg/mouse) in saline solution administered into the anterior quadriceps muscle of male and female ICR rats stimulated the response to the specific IgG antigen antibody. Testosterone levels in vaccinated males were significantly ($p=0.021$) reduced. A significant reduction was noticed in uterine implants after mating of immunized males and control females ($p=0.028$), as well as of immunized females and control males ($p=0.004$). Histological examination of gonads from both males and females in the study in week 13 showed atrophy of the seminiferous epithelium and foliclegenesis suppression.

Miller, L. A., J. P. Gionfriddo, et al. (2008). "The single-shot GnRH immunocontraceptive vaccine (GonaCon) in white-tailed deer: comparison of several GnRH preparations." *Am J Reprod Immunol* 60 (3): 214-23. It specifies that the problem lies in the requirement of a single, effective and multi-annual injection of a GnRH contraceptive agent to control reproduction of the overabundant white-tailed deer population. The study method in this investigation refers to two GnRH conjugates, GonaCon (GnRH-KLH) and GonaCon-B (GnRH-Blue® protein), which were prepared in an emulsion as immunocontraceptive vaccine formulations for a single injection and for two injections. Besides, the GnRH-KLH protein conjugate was freeze-dried and suspended in AdjuVac adjuvant to produce formulation of a fifth vaccine. Each formulation was administered to a group of captive adult female white-tailed deer. The reproductive performance of the treated females was monitored for 5 years to determine the comparative effectiveness of the different treatments. The results obtained in the study indicate that the long life of the contraceptive response (2 to 5 years) was strongly influenced by the design of the conjugated antigen, the adjuvant used, and the delivery form of the vaccine. The authors concluded that formulations in one and two injections of GonaCon and GonaCon-B produce multi-annual contraception in the adult female white-tailed deer. GonaCon-B produces a longer lasting contraceptive effect.

Sad, S., V. S. Chauhan, et al. (1993). "Synthetic gonadotrophin-releasing hormone (GnRH) vaccines incorporating GnRH and synthetic T-helper epitopes." *Vaccine* 11 (11): 1156-50. It refers to the development of a vaccine against gonadotrophin-relapsing hormone (GnRH) as an immunologic method for the treatment of prostatic hypertrophy, based on the observation that active immunization against GnRH leads to the production of anti-GnRH antibodies resulting in a reduction of the prostate gland. The authors have done research on the regulation of anti-GnRH antibody response by "carrier" molecules. In earlier studies, the authors have shown that the use of molecules of large proteins as "carriers" limits the use of said vaccines owing to the potential problems of anti-hapten of suppression induced by the carrier. In this study, the authors show that synthetic T-helper epitopes may be used as "carriers" for the generation of anti-GnRH antibody response.

However, according to the present invention, the use of immunopotentiators has allowed to obtain long term "vaccinal" effects using a single vaccine dose; therefore, the use of the antigen of the present invention in different formulations allows to modify the vaccination scheme.

BRIEF DESCRIPTION OF THE FIGURES

In FIG. 1 -■- corresponds to Control PBS and -▲- corresponds to GNRXG/Q+Adjuvant.

In FIG. 2 -■- corresponds a Control PBS and -▲- corresponds to GNRXG/Q+Adjuvant.

In FIG. 3 -■-corresponds to control PBS, -▲- corresponds to GNRXG/Q+Chi-H MW, -6.- corresponds to GNRXG/Q+Chi-L MW, and -●- corresponds to GNRXG/Q+CFA.

DETAILED DESCRIPTION OF THE INVENTION

The present invention comprises design, expression and purification of the following recombinant protein (SEQ ID NO: 1 and SEQ ID NO. 2) with a primary structure that incorporates the amino acid sequence of the gonadotrophin-releasing hormone (GnRH-I) fused to a glycosilable theoretical sequence and with immunogenic activity, that does not include pathogen or "carrier" protein sequences in its structure:

In sequences SEQ ID NO: 1 and SEQ ID NO: 2, the 10 amino acid peptide sequence of the GnRH-I hormone is observed in bold characters, fused to the 14 amino acid glycosilable theoretical sequence; this 24 amino acid chimeric peptide has been designated GnRX G/Q.

Another aspect of the invention comprises the vaccine that includes the peptide designated GnRX G/Q, to be used by itself or in a tandem repetition, the vaccine producing process, use thereof and method of mammal immunocastration.

The "theoretical" sequence may be flanking the GnRH-I sequence in any order (amino or carboxyl end of the peptide, SEQ ID NO: 1 and SEQ ID NO: 2).

Figure 6:
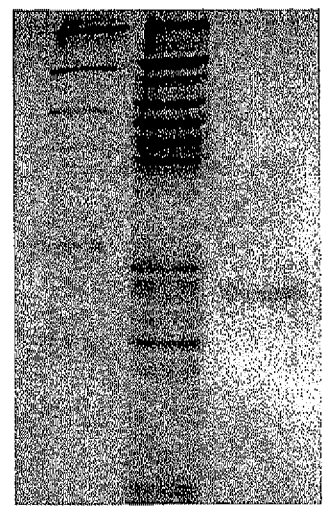
FIG. 6. 10% SOS polyacrylamide gel, where the recombinant protein designated GnRX G/Q, of the present invention, is shown tandem repeated, purified from a total extract of bacterial proteins, with an approximate weight of 29 kiloDalton

Another aspect of the invention comprises the construct, see SEQ ID NO: 3 and SEQ ID NO: 4 see sequence listing, formed by chimeric peptide GnRX G/Q tandem repeated 10 times, and observed as a recombinant protein migrating electrophoretically in a 10% SDS PAGE gel in FIG. 6.

Another aspect of the invention comprises nucleotide sequences and corresponding vectors. The nucleotide sequences were designed by inverse genetics to be used as templates in the recombinant expression of the peptide GnRX G/Q; these were inserted in prokaryotic and eukaryotic expression vectors (SEQ ID NO: 5 and SEQ ID NO: 6 see sequence listing), the result being the protein of SEQ ID NO: 7.

The present protein has been conceived as a recombinant or chimeric fusion protein where the GnRH amino acid sequence may be found as a percentage (40%) of the total molecule, the rest of the percentage (60%) corresponding to a sequence designed from the bioinformatic analysis of different peptides; a unique sequence has been designed that allows to improve immunogenicity of the segment that corresponds to the GnRH sequence, avoiding the incorporation of immunodominant segments such as pathogen, toxin or "carrier" protein-derived immunogens; this differentiates it from other molecules that have been patented in the prior art.

The designed sequence possesses a notable hydrofobicity and incorporates a consensus sequence that may be O-glycosilated in eukaryotic protein expression systems such as yeast or insect cells. This modification is oriented to improve peptide antigenicity in order to enhance the peptide capability of being recognized by the immune system. Moreover, the incorporation of this glycosilable segment differentiates the present protein from other GnRHs that incorporate fusion proteins, as the present glycopeptide is treated as a proteoglycan. Accordingly, the immune system will recognize the entire molecule as a hapten and not just as an immunogenic segment thereof.

Another aspect of the invention comprises the preparation process of the fusion protein, wherein the nucleotide sequence coding for the recombinant protein (SEQ ID NO: 5 and SEQ ID NO: 6) has been inserted in an expression vector with an inducible promoter for *E. coli* B121 bacteria (pQE 801, Qiagen) or a vector with an inducible promoter for *S. cerevisiae* yeast (pYES, invitrogen). The protein has been purified by affinity chromatography in Ni sepharose columns, which allows to eliminate possible contaminants of the expression system, mainly pyrogens, such as Lipopolysacharide (LPS).

This "theoretical" sequence has been designed using the following 10 bioinformatic algorithms that evaluate the hydrophobicity, hydrophylicity and antigenicity properties of a peptide sequence: 1) Fauchere-Pliska hydrofobicity algorithm, which generates a property profile using a hydrofobicity scale based on experimental octanol/water partitions of N-acetyl amino acid amides of each residue at a neuter pH; 2) Goldman/Engelman/Steitz hydrophylicity algorithm, which generates a property profile calculating the non-polar residues in α-helices; 3) Janin hydrofobicity algorithm, which, generates a hydrofobicity property profile based on the molar fraction of hidden or exposed residue occurrence in known proteins; 4) Kyte Doolittle hydrofobicity algorithm, which generates a hydrophobicity and hydrophylicity property profile based on Kyte Doolittle values for individual residues in inner or outer regions of a globular protein; 5) Manavalan hydrofobicity algorithm, which generates a property profile based on the hydrophobicity of an individual residue modified by the presence of other residues in an 8 angstrom radius; 6) von Heijne hydrophylicity algorithm, which generates a property profile using a scale that reflects the free transference energy estimated when a a-helix moves from an aqueous phase to a non-polar one; 7) Hopp and Woods antigenicity algorithm: Hopp-woods scale was designed to predict antigenic determinant sites in a protein, assuming that these are exposed on a protein surface and are confined to hydrophylic regions; 8) Parker antigenicity algorithm: this tool predicts the presence of antigenic determinants by the presence of areas with great local hydrophobicity, using a scale based on HPLC model peptide retention times; 9) Protrusion Index antigenicity algorithm: this tool generates a property profile using a protrusion index which is an antigenicity scale based on the study of known 3D structure proteins; and 10) Welling antigenicity algorithm: this tool calculates an antigenicity value as the log of the quotient between the percentage of a sample with known antigenic regions and the mean protein percentage.

Different amino acid sequences were evaluated for their potential capability of improving antigenicity and hydrophylicity of the sequence for GnRH-I when they are fused at the amino or carboxyl end of GnRH, as well as in tandem repetitions, comparing them to a tandem repeated GnRH-I sequence in the absence of intergenic sequences. Amino acid sequence $NH_2$-GPPFSGGGGPPFSA-COOH (amino acids 11-24 of SEQ ID NO: 1) was designed using the above mentioned parameters; it represents a hydrophobicity score in most algorithms, higher than 0 and greater than that of GnRH-I sequence. In the same way, owing to its hydrophobic condition, it exhibits limited antigenicity allowing, when analyzing the global molecule, to improve considerably GnRH-I sequence antigenicity in comparison to a tandem repeated GnRH-I sequence without intergenic sequences. Its design incorporated the consensus signal sequence SGGG (amino acids 49-52 of SEQ ID NO: 17), which corresponds to an 0-glycosilation site, susceptible of receiving this posttranslational modification when the protein is expressed in yeast or other eukaryotic cells. This tetrapeptide, which possesses the general sequence Ser-Gly-Xaa-Gly (SEQ ID NO: 18) (wherein Xaa may be any amino acid), corresponds to a recognition site for the incorporation of a glycosaminoglycan (Burdon M., et al., 1987). Finally, in the design of this sequence it was considered to exclude similarities with pathogens or "carrier" proteins. To this end, a search and alignment analysis of this sequence was conducted with databases present in GenBank using BLAST (Basic Local Alignment Search Tool) tool. In none of these sequences 1a and 1b of the present invention were present.

To manufacture and express the recombinant protein, the double strand nucleotide sequence was linked to obtain tandem repetitions and was subsequently inserted in IPTG or glucose inducible prokaryotic and eukaryotic expression vectors. The recombinant protein obtained possesses a 6-hystidine tag repetition that allows it to be purified from endogenous proteins of another host by affinity chromatography with nickel or cobalt.

Another aspect of the invention comprises those nucleotide sequences where the codon to be used in the translation is varied; these may generate the same chimeric peptide, as it may be observed in SEQ ID NO: 8, 9, 10, 11, 12, and 13 in the sequence listing.

TECHNICAL BACKGROUND OF THE INVENTION

To prove the effectiveness of the protein of the present invention, specifically that of SEQ ID NO: 7, in its capability to block steroidogenesis, oogenesis and spermatogenesis in laboratory animals via GnRH immunoneutralization, the above mentioned protein generated and purified was inoculated into laboratory animals in quantities from 50 to 500 µg in an oil adjuvant, particularly the complete or incomplete Freund's Adjuvant or an experimental adjuvant, specifically chitosan. Various parameters were analyzed such as the capability of animals to develop antibodies against the protein, their reproductive activity, spermatogenesis, oogenesis and androgen levels.

Experiment 1

The molecule as a vaccine was tested in a sample size of 18 laboratory animals, and significant differences ($p<0.01$) were obtained with regard to the expected physiologic effect and the adaptive immune response with the control group, using different adjuvants. (See FIGS. 1 to 4).

Figure 1:
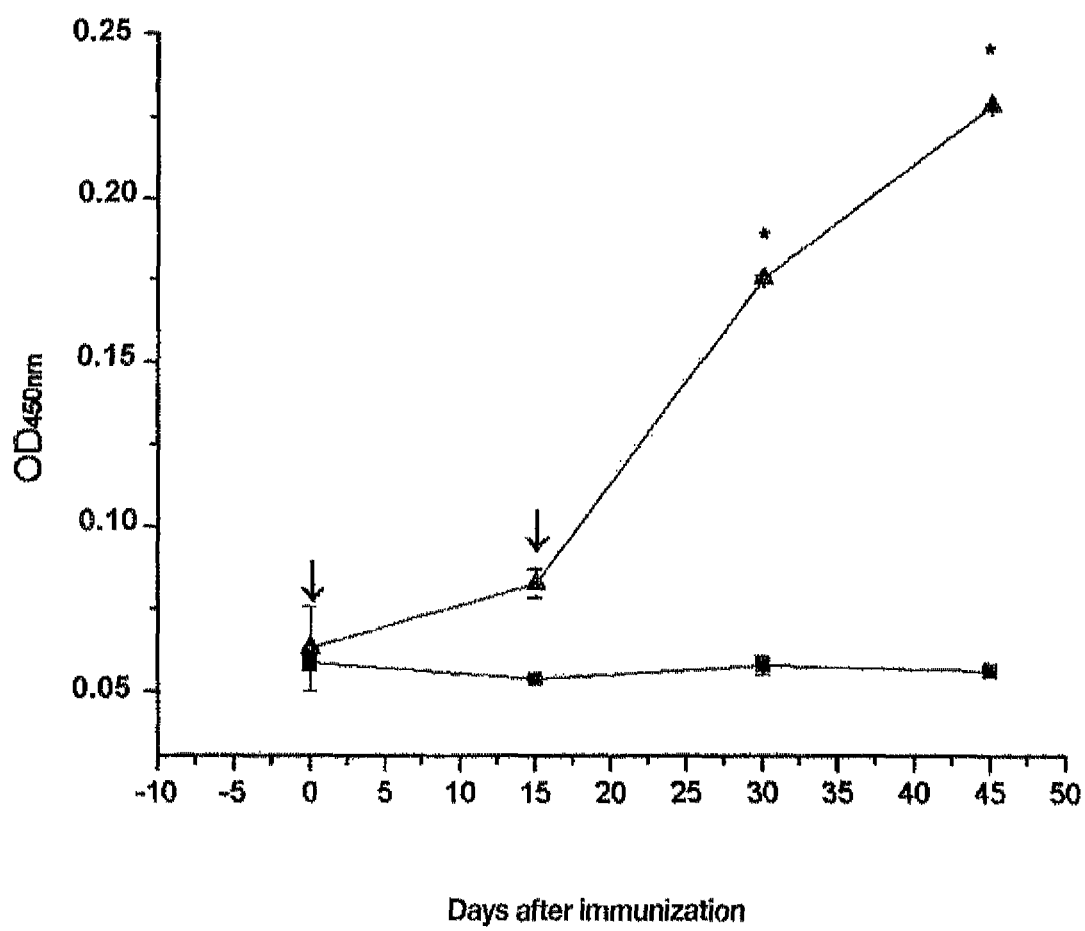
FIG. 1. Shows the immune response against the recombinant protein designated GnRXG/Q, of the present invention, measured by ELISA technique, as an increase of 19G immunoglobulins, in vaccinated animals versus control, observed as specific optic density against the recombinant peptide GnRXG/Q in immunized animals, using an aqueous adjuvant in the formulation. The serum dilution used was of 1:250 and the sample size of 10 subjects per group. The animals were immunized on days 0 and 15.
Figure 2:
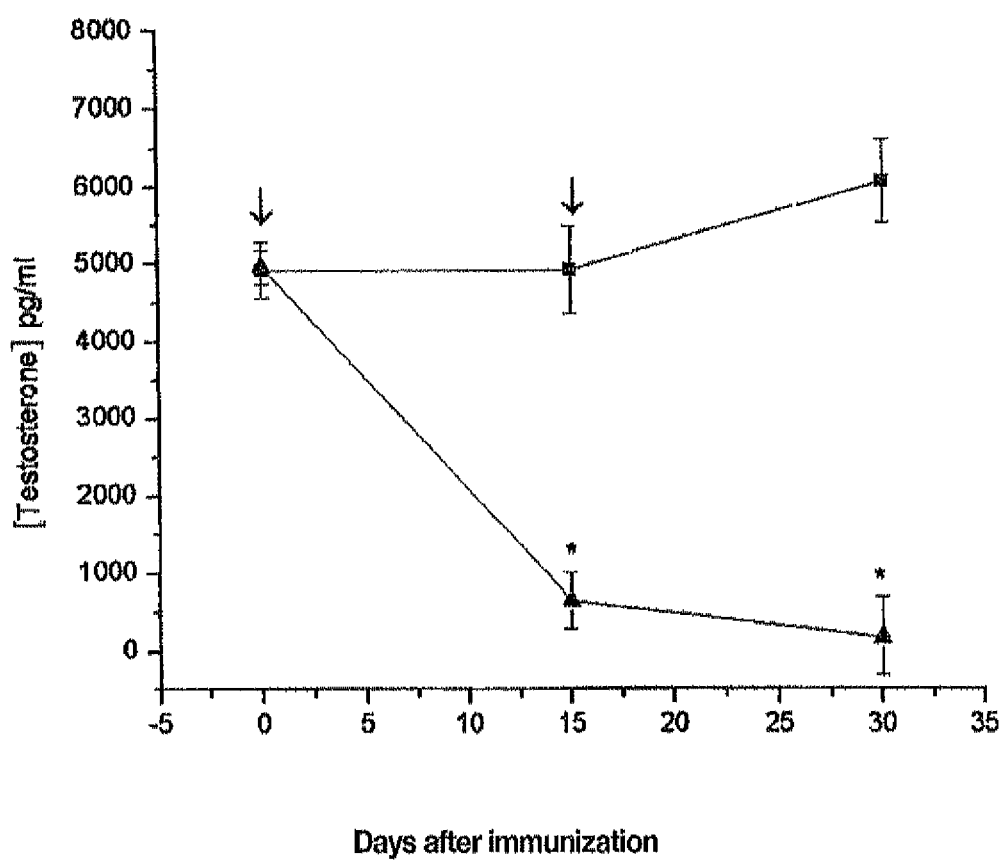
FIG. 2. Shows the decrease of testosterone serum concentration, measured by ELISA technique, in immunized animals with the recombinant protein designated GnRXG/Q, of the present invention, versus control on days 0 and 15 in a number of 10 subjects per group.
Figure 4:
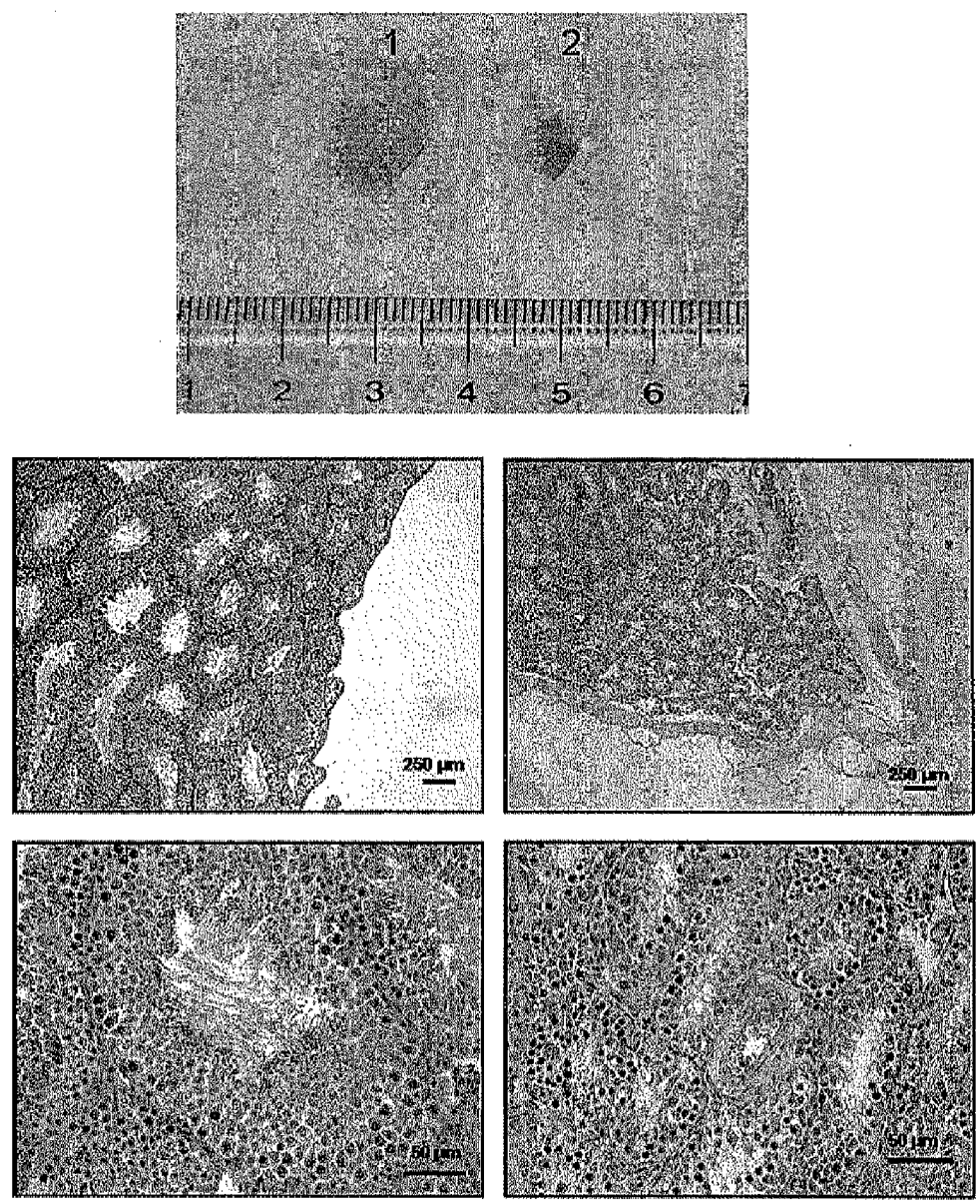
FIG. 4. Shows testicular atrophy provoked by immunization with the recombinant protein designated GnRXG/Q, of the present invention and an adjuvant in its formulation. A exhibits testicles of a control mouse (1) and of a mouse immunized with the peptide GnRX G/Q (2) a scale in centimeters may be observed in the lower portion of the photograph; B exhibits testicle histological sections under two amplification levels.

Ten 8-week-old male mice were subcutaneously immunized with 100 pg of recombinant protein GnRX G/Q (SEQ ID NO: 7) in 100 µl of a commercial adjuvant, particularly complete Freund's adjuvant, on days 0 and 15. Blood was extracted from the animals every 15 days to evaluate effectiveness of the vaccine and its capability to increase immunoglobulin titers against the GnRH-I hormone. FIG. 1 shows the increase of immunoglobulin levels specific against the GnRH-I hormone, measured by ELISA technique, of immunized animals with regard to control. FIG. 2 shows the fall in serum testosterone levels, measured by ELISA technique, of animals immunized with the above-mentioned GnRH GQ protein in comparison to a control group. At the end of the essay the animals were slaughtered and both testicles were compared macroscopically and microscopically to a group of control animals (FIG. 4).

Experiment 2

Figure 3:
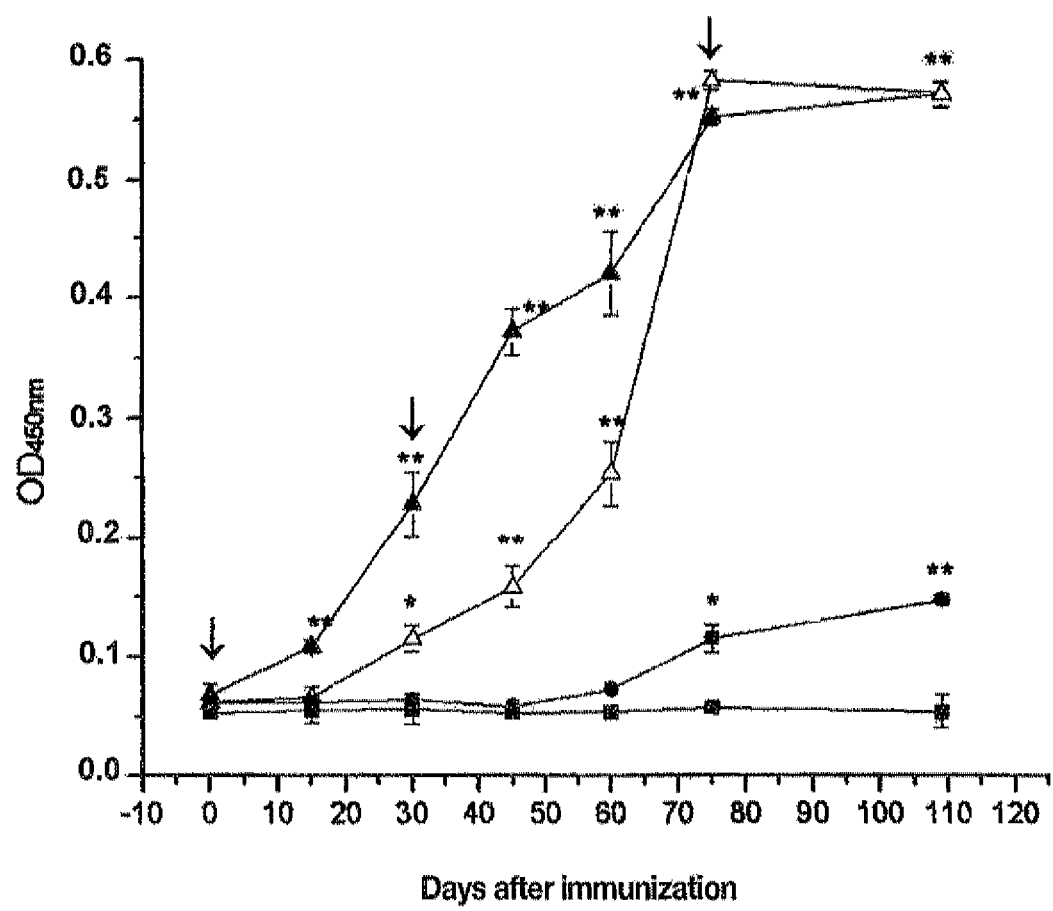
FIG. 3. Shows the immune response against the recombinant protein designated GnRXG/Q, of the present invention, as an increase of specific immunoglobulins, measured by ELISA technique, using different adjuvants in the formulation, in a 15-week assay. The animals (n=5) were immunized on days 0 and 30 and the increase in immunoglobulins was evaluated until day 110.

Fifteen 8-week old male rats, were immunized with 100 pg of recombinant protein GnRX G/Q in 200 µl of a commercial adjuvant, specifically Freund's complete adjuvant, and 2 experimental adjuvants, particularly Chitosan of high and low molecular weight, 0.5% v/v, on days 0 and 30 of the experiment. Blood was extracted from the animals every 15 days, evaluating the effect of the vaccine in the increase of immunoglobulins specific against the GnRH-I hormone in time measured by ELISA technique (FIG. 3).

Experiment 3

Figure 5:
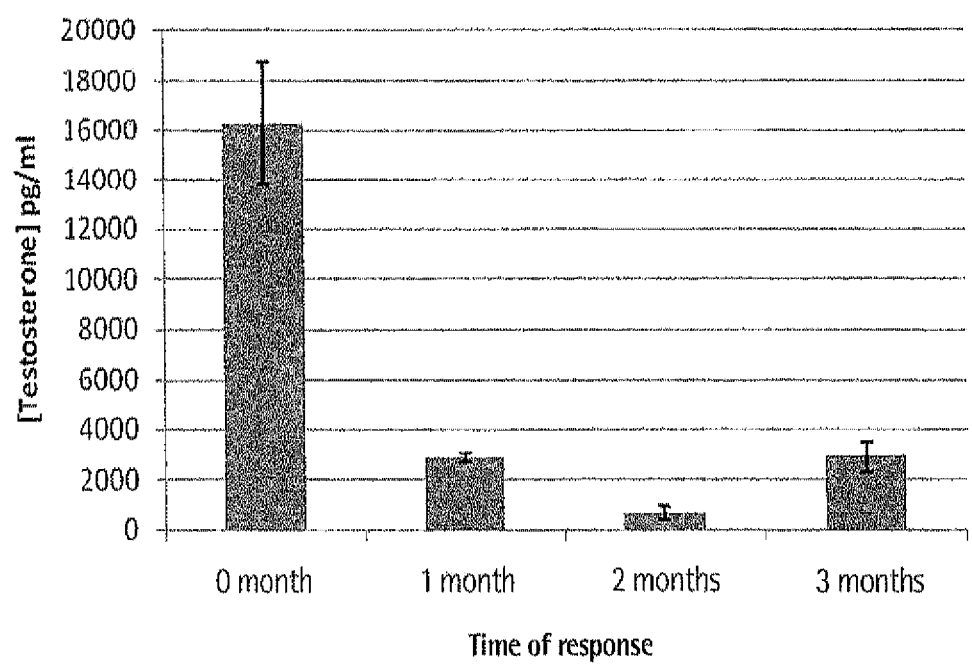
FIG. 5. Shows a decrease in testosterone serum concentration, measured by ELISA technique, in dogs immunized with the recombinant peptide designated GnRXG/Q of the present invention, in association with an adjuvant. The animals (n=7) were immunized on days 0 and 30 and the effect of the vaccine was evaluated for 3 months.

Seven adult male crossbred dogs were immunized with 200 ~g of the recombinant protein GnRX G/Q (SEQ ID NO: 7) in 1 ml of commercial adjuvant, specifically Freund's incomplete adjuvant, on days 0 and 30. Blood was extracted from the animals every 30 days to evaluate the effect of the vaccine in testosterone plasma levels. FIG. 5 shows the fall in testosterone levels in time at values approaching surgical castration (0.1 ng/ml), measured by ELISA technique.

The invention claimed is:

1. An isolated recombinant protein comprising the amino acid sequence set forth in SEQ ID NO: 15.

2. The isolated recombinant protein of claim 1, wherein said molecule is a glycoprotein.

3. An immunogenic composition comprising the isolated recombinant protein of claim 1, and a pharmaceutically acceptable carrier.

4. The immunogenic composition of claim 3, comprising between 50-500 μg of said isolated recombinant protein.

5. The immunogenic composition of claim 4, comprising between 100-200 μg of said isolated recombinant protein.

6. The immunogenic composition of claim 5, comprising 100 μg of said isolated recombinant protein.

7. The immunogenic composition of claim 6, further comprising 100 μl of said carrier.

8. The immunogenic composition of claim 6, further comprising 200 μl of said carrier.

9. The immunogenic composition of claim 6, further comprising 1 ml of said carrier.

10. The immunogenic composition of claim 5, comprising 200 μg of said isolated recombinant protein.

11. The immunogenic comprising of claim 3, comprising 100 μg of said isolated recombinant protein in 100 μl of said carrier.

12. The immunogenic composition of claim 3, comprising 100 μg of said recombinant protein in 200 μg of said carrier.

13. The immunogenic composition of claim 3, comprising 200 μl of said isolated recombinant protein in 1 ml of a carrier.

14. The immunogenic composition of claim 3, wherein said carrier is complete or incomplete Freund's adjuvant.

15. An isolated recombinant protein comprising the amino acid sequence set forth in SEQ ID NO: 16.

16. An isolated recombinant protein comprising the amino acid sequence set forth in SEQ ID NO: 7.

17. An isolated recombinant protein comprising the amino acid sequence set forth in SEQ ID NO: 14.

18. An isolated recombinant protein comprising the amino acid sequence set forth in SEQ ID NO: 17.

* * * * *

UNITED STATES PATENT AND TRADEMARK OFFICE
CERTIFICATE OF CORRECTION

PATENT NO.         : 8,940,693 B2
APPLICATION NO.    : 13/262265
DATED              : January 27, 2015
INVENTOR(S)        : Leonardo Enrique Saenz Iturriaga It is certified that error appears in the above-identified patent and that said Letters Patent is hereby corrected as shown below:

On the title page under item (12), should read --Iturriaga--

On the title page item (75) Inventor: Leonardo Enrique Saenziturriaga should be Leonardo Enrique Saenz Iturriaga Signed and Sealed this
Fifth Day of May, 2015

Michelle K. Lee
*Director of the United States Patent and Trademark Office*

SEQUENCE LISTING

```
<160> NUMBER OF SEQ ID NOS: 18

<210> SEQ ID NO 1
<211> LENGTH: 24
<212> TYPE: PRT
<213> ORGANISM: Artificial Sequence
<220> FEATURE:
<223> OTHER INFORMATION: Synthesized in the laboratory; GnRH-I fused to
      glycosilable theoretical sequence

<400> SEQUENCE: 1

Gln His Trp Ser Tyr Gly Leu Arg Pro Gly Gly Pro Pro Phe Ser Gly
1               5                   10                  15

Gly Gly Gly Pro Pro Phe Ser Ala
            20

<210> SEQ ID NO 2
<211> LENGTH: 24
<212> TYPE: PRT
<213> ORGANISM: Artificial Sequence
<220> FEATURE:
<223> OTHER INFORMATION: Synthesized in the laboratory; GnRH-I fused to
      glycosilable theoretical sequence

<400> SEQUENCE: 2

Gly Pro Pro Phe Ser Gly Gly Gly Gly Pro Pro Phe Ser Ala Gln His
1               5                   10                  15

Trp Ser Tyr Gly Leu Arg Pro Gly
            20

<210> SEQ ID NO 3
<211> LENGTH: 240
<212> TYPE: PRT
<213> ORGANISM: Artificial Sequence
<220> FEATURE:
<223> OTHER INFORMATION: Synthesized in the laboratory; Chimeric peptide
      GnRH-I fused to glycosilable theoretical sequence
      10 tandem repetitions

<400> SEQUENCE: 3

Gln His Trp Ser Tyr Gly Leu Arg Pro Gly Gly Pro Pro Phe Ser Gly
1               5                   10                  15

Gly Gly Gly Pro Pro Phe Ser Ala Gln His Trp Ser Tyr Gly Leu Arg
            20                  25                  30

Pro Gly Gly Pro Pro Phe Ser Gly Gly Gly Gly Pro Pro Phe Ser Ala
        35                  40                  45

Gln His Trp Ser Tyr Gly Leu Arg Pro Gly Gly Pro Pro Phe Ser Gly
    50                  55                  60

Gly Gly Gly Pro Pro Phe Ser Ala Gln His Trp Ser Tyr Gly Leu Arg
65                  70                  75                  80

Pro Gly Gly Pro Pro Phe Ser Gly Gly Gly Gly Pro Pro Phe Ser Ala
                85                  90                  95

Gln His Trp Ser Tyr Gly Leu Arg Pro Gly Gly Pro Pro Phe Ser Gly
            100                 105                 110

Gly Gly Gly Pro Pro Phe Ser Ala Gln His Trp Ser Tyr Gly Leu Arg
```

```
                115                 120                 125
Pro Gly Gly Pro Pro Phe Ser Gly Gly Gly Pro Pro Phe Ser Ala
        130                 135                 140

Gln His Trp Ser Tyr Gly Leu Arg Pro Gly Gly Pro Pro Phe Ser Gly
145                 150                 155                 160

Gly Gly Gly Pro Pro Phe Ser Ala Gln His Trp Ser Tyr Gly Leu Arg
                165                 170                 175

Pro Gly Gly Pro Pro Phe Ser Gly Gly Gly Gly Pro Pro Phe Ser Ala
        180                 185                 190

Gln His Trp Ser Tyr Gly Leu Arg Pro Gly Gly Pro Pro Phe Ser Gly
        195                 200                 205

Gly Gly Gly Pro Pro Phe Ser Ala Gln His Trp Ser Tyr Gly Leu Arg
        210                 215                 220

Pro Gly Gly Pro Pro Phe Ser Gly Gly Gly Gly Pro Pro Phe Ser Ala
225                 230                 235                 240

<210> SEQ ID NO 4
<211> LENGTH: 240
<212> TYPE: PRT
<213> ORGANISM: Artificial Sequence
<220> FEATURE:
<223> OTHER INFORMATION: Synthesized in the laboratory; Chimeric peptide
      GnRH-I fused to glycosilable theoretical sequence
      10 tandem repetitions

<400> SEQUENCE: 4

Gly Pro Pro Phe Ser Gly Gly Gly Pro Pro Phe Ser Ala Gln His
1               5                   10                  15

Trp Ser Tyr Gly Leu Arg Pro Gly Gly Pro Pro Phe Ser Gly Gly
            20                  25                  30

Gly Pro Pro Phe Ser Ala Gln His Trp Ser Tyr Gly Leu Arg Pro Gly
        35                  40                  45

Gly Pro Pro Phe Ser Gly Gly Gly Gly Pro Pro Phe Ser Ala Gln His
    50                  55                  60

Trp Ser Tyr Gly Leu Arg Pro Gly Gly Pro Pro Phe Ser Gly Gly Gly
65                  70                  75                  80

Gly Pro Pro Phe Ser Ala Gln His Trp Ser Tyr Gly Leu Arg Pro Gly
                85                  90                  95

Gly Pro Pro Phe Ser Gly Gly Gly Gly Pro Pro Phe Ser Ala Gln His
            100                 105                 110

Trp Ser Tyr Gly Leu Arg Pro Gly Gly Pro Pro Phe Ser Gly Gly Gly
        115                 120                 125

Gly Pro Pro Phe Ser Ala Gln His Trp Ser Tyr Gly Leu Arg Pro Gly
    130                 135                 140

Gly Pro Pro Phe Ser Gly Gly Gly Gly Pro Pro Phe Ser Ala Gln His
145                 150                 155                 160

Trp Ser Tyr Gly Leu Arg Pro Gly Gly Pro Pro Phe Ser Gly Gly Gly
                165                 170                 175

Gly Pro Pro Phe Ser Ala Gln His Trp Ser Tyr Gly Leu Arg Pro Gly
            180                 185                 190

Gly Pro Pro Phe Ser Gly Gly Gly Gly Pro Pro Phe Ser Ala Gln His
        195                 200                 205

Trp Ser Tyr Gly Leu Arg Pro Gly Gly Pro Pro Phe Ser Gly Gly Gly
    210                 215                 220

Gly Pro Pro Phe Ser Ala Gln His Trp Ser Tyr Gly Leu Arg Pro Gly
225                 230                 235                 240
```

<210> SEQ ID NO 5
<211> LENGTH: 72
<212> TYPE: DNA
<213> ORGANISM: Artificial Sequence
<220> FEATURE:
<223> OTHER INFORMATION: Synthesized in the laboratory; encoding GnRH-I
      sequence fused to glycosilable theoretical sequence

<400> SEQUENCE: 5
cagcactgga gctacggcct gcgccccggc ggcccccct tcagcggcgg cggcggcccc    60
cccttcagtg ca                                                       72

<210> SEQ ID NO 6
<211> LENGTH: 72
<212> TYPE: DNA
<213> ORGANISM: Artificial Sequence
<220> FEATURE:
<223> OTHER INFORMATION: Synthesized in the laboratory; encoding GnRH-I
      sequence fused to glycosilable theoretical sequence

<400> SEQUENCE: 6 ggcccccct tcagcggcgg cggcggcccc cccttcagcg cccagcactg gagctacggc    60
ctgcgccccg gc                                                       72

<210> SEQ ID NO 7
<211> LENGTH: 48
<212> TYPE: PRT
<213> ORGANISM: Artificial Sequence
<220> FEATURE:
<223> OTHER INFORMATION: Synthesized in the laboratory; protein
      resulting from expressing prokaryotic and eukaryotic vectors

<400> SEQUENCE: 7

Gln His Trp Ser Tyr Gly Leu Arg Pro Gly Gly Pro Pro Phe Ser Gly
1               5                   10                  15

Gly Gly Gly Pro Pro Phe Ser Gly Gln His Trp Ser Tyr Gly Leu Arg
            20                  25                  30

Pro Gly Gly Pro Pro Phe Ser Gly Gly Gly Gly Pro Pro Phe Ser Gly
        35                  40                  45

<210> SEQ ID NO 8
<211> LENGTH: 72
<212> TYPE: DNA
<213> ORGANISM: Artificial Sequence
<220> FEATURE:
<223> OTHER INFORMATION: Synthesized in the laboratory; nucleotide
      sequence using a specific codon in the translation to generate
      a specific chimeric peptide

<400> SEQUENCE: 8
cagcactggt cctacggtct gcgtccgggt ggtccgccgt tctccggtgg tggtggtccg    60
ccgttctccg ct                                                       72

<210> SEQ ID NO 9
<211> LENGTH: 72
<212> TYPE: DNA
<213> ORGANISM: Artificial Sequence
<220> FEATURE:
<223> OTHER INFORMATION: Synthesized in the laboratory; nucleotide
      sequence using a specific codon in the translation to generate
      a specific chimeric peptide

<400> SEQUENCE: 9

```
caacactggt cttacggttt gagaccaggt ggtccaccat tctctggtgg tggtggtcca    60
ccattctctg ct                                                       72
```

<210> SEQ ID NO 10
<211> LENGTH: 72
<212> TYPE: DNA
<213> ORGANISM: Artificial Sequence
<220> FEATURE:
<223> OTHER INFORMATION: Synthesized in the laboratory; nucleotide
      sequence using a specific codon in the translation to generate
      a specific chimeric peptide

<400> SEQUENCE: 10

```
cagcactggt cctacggcct ccgcccgggc ggcccgccgt tctccggcgg cggcggcccg    60
ccgttctccg cc                                                       72
```

<210> SEQ ID NO 11
<211> LENGTH: 72
<212> TYPE: DNA
<213> ORGANISM: Artificial Sequence
<220> FEATURE:
<223> OTHER INFORMATION: Synthesized in the laboratory; nucleotide
      sequence using a specific codon in the translation to generate
      a specific chimeric peptide

<400> SEQUENCE: 11

```
cagcactggt cctacggtct gcgtccgggt ggtccgccgt tctccggtgg tggtggtccg    60
ccgttctccg gt                                                       72
```

<210> SEQ ID NO 12
<211> LENGTH: 72
<212> TYPE: DNA
<213> ORGANISM: Artificial Sequence
<220> FEATURE:
<223> OTHER INFORMATION: Synthesized in the laboratory; nucleotide
      sequence using a specific codon in the translation to generate
      a specific chimeric peptide

<400> SEQUENCE: 12

```
cagcactggt cctacggcct ccgcccgggc ggcccgccgt tctccggcgg cggcggcccg    60
ccgttctccg gc                                                       72
```

<210> SEQ ID NO 13
<211> LENGTH: 72
<212> TYPE: DNA
<213> ORGANISM: Artificial Sequence
<220> FEATURE:
<223> OTHER INFORMATION: Synthesized in the laboratory; nucleotide
      sequence using a specific codon in the translation to generate
      a specific chimeric peptide

<400> SEQUENCE: 13

```
caacactggt cttacggttt gagaccaggt ggtccaccat tctctggtgg tggtggtcca    60
ccattctctg gt                                                       72
```

<210> SEQ ID NO 14
<211> LENGTH: 14
<212> TYPE: PRT
<213> ORGANISM: Artificial Sequence
<220> FEATURE:
<223> OTHER INFORMATION: Synthesized in the laboratory; peptide
      encoded by a nucleotide sequence using a specific codon in the
      translation to generate a specific chimeric peptide

<400> SEQUENCE: 14

```
Gly Pro Pro Phe Ser Gly Gly Gly Pro Pro Phe Ser Ala
1               5                   10

<210> SEQ ID NO 15
<211> LENGTH: 48
<212> TYPE: PRT
<213> ORGANISM: Artificial Sequence
<220> FEATURE:
<223> OTHER INFORMATION: Synthesized in the laboratory; fusion protein
      of two peptides consisting of GnRH-I fused to a theoretical
      glycosilable sequence

<400> SEQUENCE: 15

Gln His Trp Ser Tyr Gly Leu Arg Pro Gly Pro Pro Phe Ser Gly
1               5                   10                  15

Gly Gly Gly Pro Pro Phe Ser Ala Gly Pro Pro Phe Ser Gly Gly Gly
            20                  25                  30

Gly Pro Pro Phe Ser Ala Gln His Trp Ser Tyr Gly Leu Arg Pro Gly
        35                  40                  45

<210> SEQ ID NO 16
<211> LENGTH: 72
<212> TYPE: PRT
<213> ORGANISM: Artificial Sequence
<220> FEATURE:
<223> OTHER INFORMATION: Synthesized in the laboratory; fusion protein
      consisting of two copies of SEQ ID NO: 1, and one copy of
      SEQ ID NO: 2

<400> SEQUENCE: 16

Gln His Trp Ser Tyr Gly Leu Arg Pro Gly Pro Pro Phe Ser Gly
1               5                   10                  15

Gly Gly Gly Pro Pro Phe Ser Ala Gln His Trp Ser Tyr Gly Leu Arg
            20                  25                  30

Pro Gly Gly Pro Pro Phe Ser Gly Gly Gly Pro Pro Phe Ser Ala
        35                  40                  45

Gly Pro Pro Phe Ser Gly Gly Gly Gly Pro Pro Phe Ser Ala Gln His
    50                  55                  60

Trp Ser Tyr Gly Leu Arg Pro Gly
65                  70

<210> SEQ ID NO 17
<211> LENGTH: 52
<212> TYPE: PRT
<213> ORGANISM: Artificial Sequence
<220> FEATURE:
<223> OTHER INFORMATION: Synthesized in the laboratory; SEQ ID NO: 15,
      followed by 4 additional amino acids

<400> SEQUENCE: 17

Gln His Trp Ser Tyr Gly Leu Arg Pro Gly Pro Pro Phe Ser Gly
1               5                   10                  15

Gly Gly Gly Pro Pro Phe Ser Ala Gly Pro Pro Phe Ser Gly Gly Gly
            20                  25                  30

Gly Pro Pro Phe Ser Ala Gln His Trp Ser Tyr Gly Leu Arg Pro Gly
        35                  40                  45

Ser Gly Gly Gly
    50

<210> SEQ ID NO 18
<211> LENGTH: 4
<212> TYPE: PRT
```

```
<213> ORGANISM: Artificial Sequence
<220> FEATURE:
<223> OTHER INFORMATION: Synthesized in the laboratory
<220> FEATURE:
<221> NAME/KEY: Misc_feature
<222> LOCATION: (3)..(3)
<223> OTHER INFORMATION: Xaa is any amino acid

<400> SEQUENCE: 18

Ser Gly Xaa Gly
1
```